(12) United States Patent
Larsson

(10) Patent No.: US 11,802,374 B2
(45) Date of Patent: Oct. 31, 2023

(54) METHOD OF DETERMINING THE MOISTURE CONTENT OF A WEB OF CELLULOSE PULP

(71) Applicant: ANDRITZ TECHNOLOGY AND ASSET MANAGEMENT GMBH, Graz (AT)

(72) Inventor: Ola Larsson, Vaxjo (SE)

(73) Assignee: ANDRITZ TECHNOLOGY AND ASSET MANAGEMENT GMBH, Graz (AT)

( * ) Notice: Subject to any disclaimer, the term of this patent is extended or adjusted under 35 U.S.C. 154(b) by 443 days.

(21) Appl. No.: 17/279,897

(22) PCT Filed: Sep. 24, 2019

(86) PCT No.: PCT/EP2019/075722
§ 371 (c)(1),
(2) Date: Mar. 25, 2021

(87) PCT Pub. No.: WO2020/064738
PCT Pub. Date: Apr. 2, 2020

(65) Prior Publication Data
US 2022/0034037 A1    Feb. 3, 2022

(30) Foreign Application Priority Data
Sep. 25, 2018 (SE) .................... 1851138-6

(51) Int. Cl.
*D21F 5/00* (2006.01)
*D21F 5/18* (2006.01)
(Continued)

(52) U.S. Cl.
CPC ............. *D21F 5/185* (2013.01); *D21F 7/003* (2013.01); *G01N 33/346* (2013.01)

(58) Field of Classification Search
CPC ........ D21F 5/185; D21F 7/003; G01N 33/346
(Continued)

(56) References Cited

U.S. PATENT DOCUMENTS

| 6,440,270 B1 | 8/2002 | Haapanen |
| 6,792,331 B1 | 9/2004 | Hamström et al. |
| 2005/0145357 A1 | 7/2005 | Muench et al. |

FOREIGN PATENT DOCUMENTS

| EP | 1517207 A2 | 3/2005 |
| WO | 0250370 A1 | 6/2002 |

(Continued)

OTHER PUBLICATIONS

Search Report for FI 20215468 prepared by the Finnish Patent and Registration Office, dated Sep. 1, 2022, 1 page.

(Continued)

*Primary Examiner* — Mark Halpern
(74) *Attorney, Agent, or Firm* — BROOKS KUSHMAN PC; John E. Nemazi

(57) ABSTRACT

The present invention relates to a method of determining the moisture content of a web of cellulose pulp arriving at a pulp dryer. The method comprises measuring, at several instants during a predetermined time interval, the moisture content of said web using a moisture sensor arranged upstream of the pulp dryer; measuring state variables of drying medium of said pulp dryer; calculating, based on said moisture sensor measurements, a total value of moisture introduced into the pulp dryer by a portion of said web during said predetermined time interval; determining, based on said measured state variables, a predicted total value of moisture present inside the pulp dryer; comparing said calculated total value with said predicted total value to obtain a deviation therebetween; calibrating said moisture sensor using said devia- (Continued)

tion; and measuring the moisture content of a web of cellulose pulp using said calibrated moisture sensor.

6 Claims, 2 Drawing Sheets

(51) Int. Cl.
   *D21F 7/00* (2006.01)
   *G01N 33/34* (2006.01)
(58) Field of Classification Search
   USPC .......................................................... 162/198
   See application file for complete search history.

(56) References Cited

FOREIGN PATENT DOCUMENTS

| WO | 03004764 A1 | 1/2003 |
| WO | 2006/051157 A2 | 5/2006 |

OTHER PUBLICATIONS

Communication of Acceptance for FI 20215468 prepared by the Finnish Patent and Registration Office, dated Aug. 31, 2022, 4 pages.
International Search Report and Written Opinion for Application No. PCT/EP2019/075722, dated Dec. 13, 2019, 12 Pages.

METHOD OF DETERMINING THE MOISTURE CONTENT OF A WEB OF CELLULOSE PULP

CROSS-REFERENCE TO RELATED APPLICATION

This application is the U.S. national phase of PCT Application No. PCT/EP2019/075722 filed on Sep. 24, 2019, which claims priority to Swedish Patent Application No. 11851138-6, filed Sep. 25, 2018, which are incorporated herein by reference in their entireties.

TECHNICAL FIELD

The present invention relates to a method of determining the moisture content of a web of cellulose pulp arriving at a pulp dryer.

BACKGROUND

Cellulose pulp is often dried in a dryer having several superposed horizontal drying decks. Cellulose pulp having about 50% water content is fed into the pulp dryer. A web of cellulose pulp is conveyed across the drying decks of the dryer. Dry cellulose pulp, having about 10% water content, is outputted at the end of the lowest drying deck.

An example of a cellulose pulp dryer is illustrated in WO 2012/074462 A1. Hot gas in the form of hot air is blown onto a web of cellulose pulp by means of upper blow boxes and lower blow boxes. The air blown by the blow boxes transfer heat to the web to dry it. In addition, the air blown by the lower blow boxes keeps the web floating above the lower blow boxes. Hot air is supplied to the blow boxes by means of a circulation air system comprising fans and steam radiators heating the drying air.

In order to control the drying process different parameters are measured. Such a parameter is the moisture content of the web that is conveyed into the pulp dryer. Typically, the moisture content is measured using a moisture sensor.

However, the accuracy of known moisture sensors is considered to be insufficient. Hence, there is a need for a more accurate measuring of the moisture content of a web arriving at a pulp dryer.

SUMMARY

It is an object of the present invention to provide a more accurate method of determining the moisture content of a web of cellulose pulp arriving at a pulp dryer.

This and other objects that will be apparent from the following summary and description are achieved by a method according to the appended claims.

According to one aspect of the present disclosure there is provided a method of determining the moisture content of a web of cellulose pulp arriving at a pulp dryer, said method comprising measuring, at several instants during a predetermined time interval, the moisture content of said web using a moisture sensor arranged upstream of the pulp dryer; measuring state variables of drying medium of said pulp dryer; calculating, based on said moisture sensor measurements, a total value of moisture introduced into the pulp dryer by a portion of said web during said predetermined time interval; determining, based on said measured state variables, a predicted total value of moisture present inside the pulp dryer; comparing said calculated total value with said predicted total value to obtain a deviation therebetween; calibrating said moisture sensor using said deviation; and measuring the moisture content of a web of cellulose pulp using said calibrated moisture sensor.

A pulp dryer may be seen as a thermodynamic system, which allows the moisture content inside the dryer to be calculated at each instant with high accuracy using energy and/or mass calculations based on measured state variables of drying medium of the pulp dryer. The method of the present disclosure is based on the idea of using the results from such calculations to calibrate a moisture sensor arranged upstream, e.g. at the entry, of a pulp dryer.

By calibrating the moisture sensor in this manner a more accurate determination of the moisture content of a pulp web arriving at the dryer is achieved. This provides for a more efficient control of the drying process. Furthermore, it makes it possible to detect deviations occurring upstream of the pulp dryer and to adapt drying conditions in accordance therewith to take them into consideration. Hence, since the moisture content determined by the calibrated sensor is reliable it can be used for different purposes with respect to the overall efficiency of the pulp dryer. For instance, energy consumption and/or pulp quality may be optimized.

The method thus allows for quick and reliable detection of deviations and variations in moisture contents. As the calibrated moisture sensor provides a reliable measurement of the moisture content of pulp web arriving at the pulp dryer, it may be used to optimize the drying efficiency and/or detect deviations upstream of the the pulp dryer at an early stage.

In the calculations of the predicted total content of moisture inside the pulp dryer, state variables such as drying medium pressure, drying medium temperature drying medium flow, steam pressure, steam temperature, steam flow, pulp web temperature, pulp web flow and moisture content of the dried pulp web may be used.

The predetermined time interval may vary and depends on the speed at which the pulp web is fed into the pulp dryer. Furthermore, a certain time interval may be used during start-up of a drying process whereas a different time interval may be used during normal operation of the pulp dryer.

Preferably, said step of measuring state variables comprises measuring at least incoming drying gas conditions and exhaust gas conditions.

Said step of measuring state variables of drying medium of the pulp dryer and said step of determining a predicted total value of moisture present inside the pulp dryer may be performed at least once during said predetermined time interval.

Preferably, said step of measuring state variables of drying medium of the pulp dryer and said step of determining a predicted total value of moisture present inside the pulp dryer are carried out at several instants during said predetermined time interval.

Calibration of the moisture sensor may be carried out on a regularly basis in order to control the operation of a pulp dryer in an efficient manner over time during an operating cycle. For instance, calibration of the moisture sensor may be carried out several times a day.

These and other aspects of the invention will be apparent from and elucidated with reference to the claims and the embodiments described hereinafter.

BRIEF DESCRIPTION OF THE DRAWINGS

The invention will now be described in more detail with reference to the appended drawings in which.

DETAILED DESCRIPTION

Figure 1:
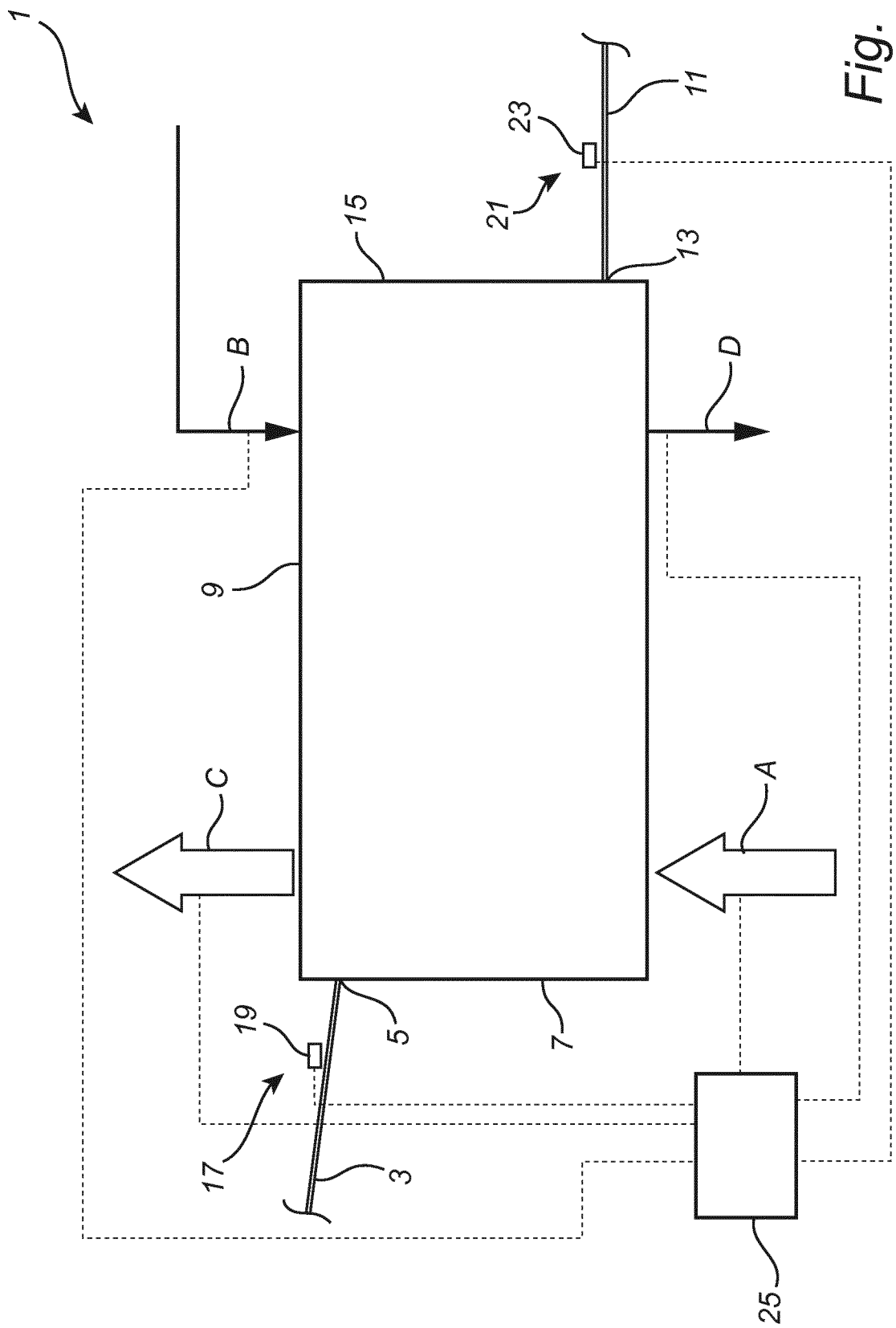
FIG. 1 is a schematic view and illustrates a dryer for drying cellulose pulp.

FIG. 1 illustrates in a schematic manner a cellulose pulp dryer 1 for drying cellulose pulp in accordance with the air borne web principle where cellulose pulp is dried by means of hot air while travelling along horizontal drying sections of the pulp dryer 1. The dryer 1 thus utilizes heated air to dry and support the pulp web. Typically, a dryer 1 would comprise 4-40 drying decks. Large dryers may even comprise 50 drying decks or more.

A wet pulp web 3 enters the dryer 1 at a known speed via an inlet 5 arranged in a first side wall 7 of the pulp dryer housing 9. In the pulp dryer of FIG. 1, the inlet 5 is arranged in the upper portion of side wall 7, but the inlet may, in an alternative dryer, be arranged in the lower portion of the first side wall 7. The web 3 is forwarded horizontally towards the right in the dryer 1 until the web 3 reaches a turning roll (not shown). The web 3 is turned around the turning roll, and then travels horizontally towards the left until the web 3 reaches a subsequent turning roll at which the web 3 is turned again. In this manner the web 3 is fed through the housing 9 from the inlet 5 and travels, in a zigzag manner at a set speed, from the top to the bottom of the dryer 1. The dried web 11 leaves the dryer 1 via an outlet 13 arranged in a second side wall 15 of the pulp dryer housing 9. In the pulp dryer of FIG. 1, the outlet 13 is arranged in the lower portion of the second side wall 15, but the outlet 13 may, in an alternative embodiment, be arranged in the upper portion of the second side wall 15.

Blow boxes (not shown) for drying the web are arranged in each of the drying decks of the dryer 1. Heated air is supplied to the blow boxes of the dryer 1 through an air inlet, as schematically illustrated by arrow A in FIG. 1. The drying air may, e.g., be heated by conducting it through a bank of boilers heated with steam. To this end, steam for heating the drying air is fed to the pulp dryer 1, as schematically illustrated by arrow B in FIG. 1.

Exhaust air is removed from the pulp dryer 1 through an air outlet, as schematically illustrated by arrow C in FIG. 1, and steam condensate is removed from the pulp dryer 1 as schematically illustrated by arrow D in FIG. 1.

Typically air of a temperature of 80 to 250° C. is utilized for the drying process. The cellulose pulp web 3 entering the dryer 1 typically has a dry solids content of 40-60% by weight, and the cellulose pulp web 3 leaving the dryer 1 has a dry solids content of typically 85-95% by weight. The cellulose pulp web 11 leaving the dryer 1 typically has a basis weight of 800 to 1500 g/m$^2$, when measured at a moisture content of 0.11 kg water per kg dry substance, and a thickness of 0.8 to 3 mm.

At the pulp web inlet 5, a moisture measurement unit 17 capable of measuring dry solids content of the pulp web 3 fed into the pulp dryer 1 is arranged. The moisture measurement unit 17 comprises a moisture sensor 19, e.g. in the form of an IR moisture sensor or a sensor using another measurement principle. The moisture sensor may be either a stationary sensor or a traversing sensor arranged to move across the direction of travel of the pulp web 3.

At the web outlet 13, a web condition monitoring unit 21 comprising a second moisture sensor 23 is arranged to measure the moisture content of dried web 11. The web condition monitoring 17 unit is also capable of measuring temperature and flow of dried pulp web 11.

During operation of the pulp dryer 1 several state variables are measured in a conventional manner. A control unit 25 is arranged to receive information from several measurement units, as schematically illustrated by dotted lines in FIG. 1. Typically, inlet air conditions, exhaust air conditions, inlet steam conditions, outlet steam/condensate conditions and pulp outlet conditions are measured and transmitted to the control unit 25 regularly during operation of the pulp dryer 1.

For instance, state variables such as incoming drying air pressure, incoming drying air temperature, incoming drying air flow, exhaust air pressure, exhaust air temperature and exhaust air flow may be measured and used to calculate the predicted amount of moisture inside the pulp dryer 1. Also, state variables such as incoming steam pressure, incoming steam temperature, incoming steam flow, outgoing steam/condensate pressure, outgoing steam/condensate temperature and outgoing steam/condensate flow may be measured and used to calculate the predicted amount of moisture inside the pulp dryer 1.

Also, state variables in the form of temperature, flow and moisture content of the dried web may be measured and used to calculate the predicted amount of moisture inside the pulp dryer 1.

Figure 2:
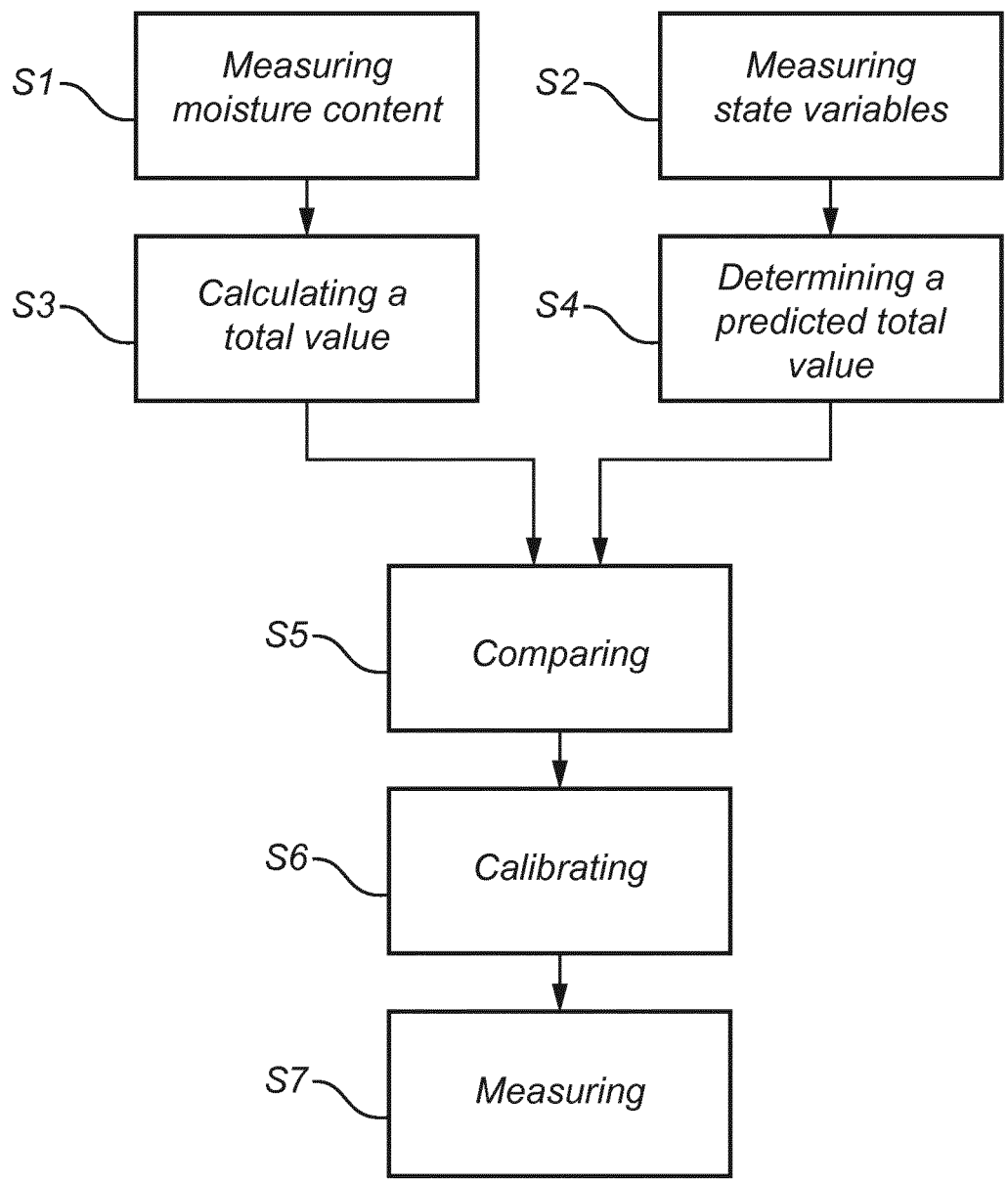
FIG. 2 illustrates steps of a method according to an embodiment of the present disclosure.

With reference to FIG. 1 and FIG. 2, a method of determining the moisture content of a web 3 of cellulose pulp arriving at the pulp dryer 1 will now be described.

In a first measuring step S1, the moisture content of a cellulose pulp web 3 arriving at the pulp dryer 1 is measured using the moisture sensor 19 of the moisture measurement unit 17. The moisture content of the web 3 is measured at several instants during a predetermined time interval. Measurements carried out by the moisture sensor 19 are transmitted to the control unit 25.

In a second measuring step S2, state variables are measured. Typically, state variables, such as, e.g., incoming drying air conditions and exhaust air conditions are measured regularly during operation of the pulp dryer 1. Also, state variables of steam heating the drying air and state variables of the dried web 11 leaving the pulp dryer 1 are measured regularly.

In a calculating step S3, a total value of moisture introduced into the pulp dryer 1 by a portion of the web 3 during the predetermined time interval is calculated by the control unit 25 based on the moisture content measurements carried out by the moisture sensor 19 in step S1 and actual web speed. In this step, a calculated total value is thus established.

In a determining step S4, a predicted total value of moisture present inside the pulp dryer is determined. The predicted total value is determined using mass- and/or energy balance calculations based on measurements carried out in the second measuring step S2. The predicted total value is determined at at least one instant during the predetermined time interval. The pulp dryer 1 is thus seen as a thermodynamic system, which allows the total amount of moisture present inside the dryer 1 at each instant to be determined with high precision based on measurements of state variables.

Hence, temperatures, pressures and flows of the fed and exhausted drying medium, i.e. in this case heated air, may be measured and used to calculate the total amount of moisture present inside the pulp dryer by means of mass and/or energy balance calculations.

Optionally, measured conditions of the steam heating the drying medium, such as e.g. steam pressure, steam temperature and steam flow, and/or measured conditions, such as temperature, pressure and moisture content of the dried pulp web 11 measured by means of the web condition monitoring unit 21 may be used when determining a predicted total value of moisture present inside the pulp dryer, which may further improve the accuracy of the determination.

After carrying out above mentioned steps S1-S4, in a comparing step S5, the calculated total value of moisture present inside the pulp dryer 1 is compared with the predicted total value of moisture present inside the pulp dryer 1 to obtain a deviation therebetween.

Then, in a calibrating step S6, the moisture sensor 19 of the moisture measurement unit 17 is calibrated using the deviation between the calculated total value of moisture and the predicted total value of moisture.

Finally, in a third measuring step S7, the moisture content of a web 3 arriving at the pulp dryer 1 is measured using the calibrated moisture sensor 19.

The moisture sensor 19 may be calibrated in this way regularly, e.g. several times a day. The measurements used to calibrate the moisture sensor 19 are carried out prior to such a calibration operation.

The person skilled in the art realizes that the present invention by no means is limited to the embodiments described above. On the contrary, many modifications and variations are possible within the scope of the appended claims.

With reference to FIG. 1, it has been described that the method according to the present disclosure may be used for determining the moisture content of a web of cellulose pulp arriving at a pulp dryer for drying cellulose pulp in accordance with the air borne web principle. It is however appreciated that the method may be used for determining the moisture content of a web of cellulose pulp arriving at other types of pulp dryers, such as, e.g. a pulp dryer comprising steam heated cylinders.

The invention claimed is:

1. A method of determining the moisture content of a web of cellulose pulp arriving at a pulp dryer, said method comprising:

measuring the moisture content of said web at several instants during a predetermined time interval using a moisture sensor arranged upstream of the pulp dryer;

measuring state variables of drying medium of said pulp dryer;

characterized by further comprising:

calculating, based on said moisture sensor measurements, a total value of moisture introduced into the pulp dryer by a portion of said web during said predetermined time interval;

determining, based on said measured state variables, a predicted total value of moisture present inside the pulp dryer;

comparing said calculated total value with said predicted total value to obtain a deviation therebetween;

calibrating said moisture sensor using said deviation; and measuring the moisture content of a web of cellulose pulp using said calibrated moisture sensor.

2. The method according to claim 1, wherein said predicted total value is determined using mass and/or energy balance calculations.

3. The method according to claim 1, wherein the step of measuring state variables comprises measuring at least incoming gas conditions and exhaust gas conditions.

4. The method according to claim 1, wherein said step of measuring state variables of drying medium of the pulp dryer and said step of determining a predicted total value of moisture present inside the pulp dryer are carried out at least once during said predetermined time interval.

5. The method according to claim 1, wherein said step of measuring state variables of drying medium of the pulp dryer and said step of determining a predicted total value of moisture present inside the pulp dryer are carried out at several instants during said predetermined time interval.

6. The method according to claim 1, wherein said step of calibrating the moisture sensor is carried out several times a day.

* * * * *